(12) United States Patent
Wei

(10) Patent No.: US 11,524,124 B2
(45) Date of Patent: Dec. 13, 2022

(54) DRUG DELIVERY DEVICE

(71) Applicant: Min Wei, Carmel, IN (US)

(72) Inventor: Min Wei, Carmel, IN (US)

(73) Assignee: Min Wei, Carmel, IN (US)

( * ) Notice: Subject to any disclaimer, the term of this patent is extended or adjusted under 35 U.S.C. 154(b) by 506 days.

(21) Appl. No.: 16/699,002

(22) Filed: Nov. 28, 2019

(65) Prior Publication Data

US 2020/0179612 A1 Jun. 11, 2020

Related U.S. Application Data

(60) Provisional application No. 62/777,079, filed on Dec. 8, 2018.

(51) Int. Cl.
*A61M 5/32* (2006.01)
*A61M 5/315* (2006.01)
*A61M 5/31* (2006.01)

(52) U.S. Cl.
CPC ........ *A61M 5/3202* (2013.01); *A61M 5/3157* (2013.01); *A61M 5/31571* (2013.01); *A61M 5/31578* (2013.01); *A61M 2005/3115* (2013.01); *A61M 2205/50* (2013.01)

(58) Field of Classification Search
CPC .............. A61M 5/3202; A61M 5/3157; A61M 5/31571; A61M 5/31578; A61M 2005/3115; A61M 2205/50
See application file for complete search history.

(56) References Cited

U.S. PATENT DOCUMENTS

| | | | |
|---|---|---|---|
| 2010/0211005 A1* | 8/2010 | Edwards | A61P 19/02 604/82 |
| 2020/0030546 A1* | 1/2020 | Cirillo | A61M 5/20 |

\* cited by examiner

*Primary Examiner* — Tasnim Mehjabin Ahmed
(74) *Attorney, Agent, or Firm* — Min Wei

(57) ABSTRACT

A drug delivery device comprises a medication container containing medication for delivery and a detachable unit having an electronic circuit with a microprocessor. The electronic circuit is open and non-operational when the detachable component is assembled on the drug delivery device; and the electronic circuit is closed and operational when the detachable component is detached from the drug delivery device. The detachment of the detachable unit is an essential step to operate the drug delivery device. The detachable unit can be an activation protection cap or a needle shield remover for an autoinjector device. Alternatively, the detachable unit can be a needle shield remover for a pre-filled syringe.

19 Claims, 8 Drawing Sheets

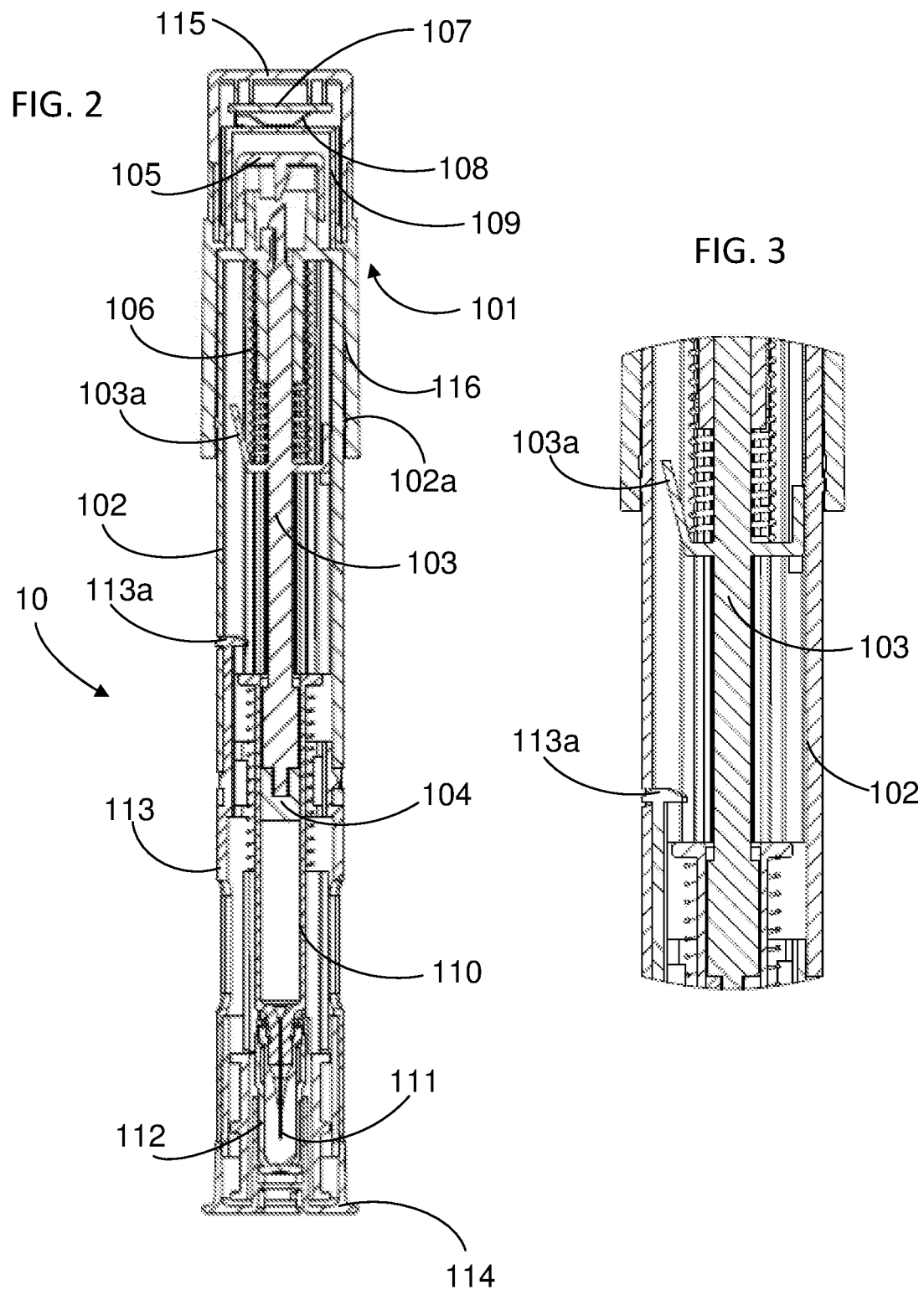

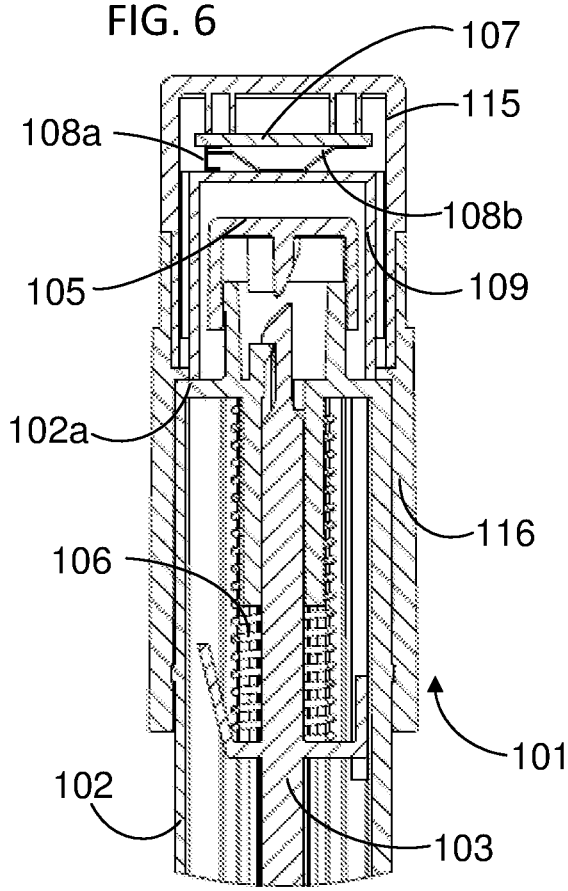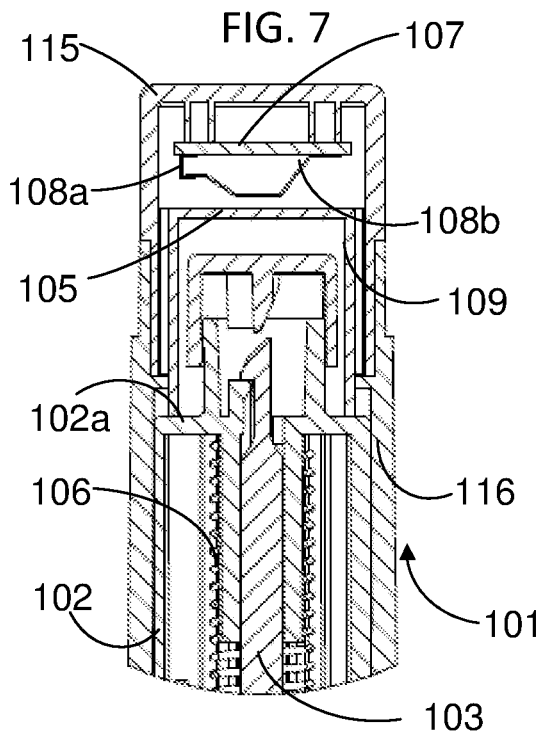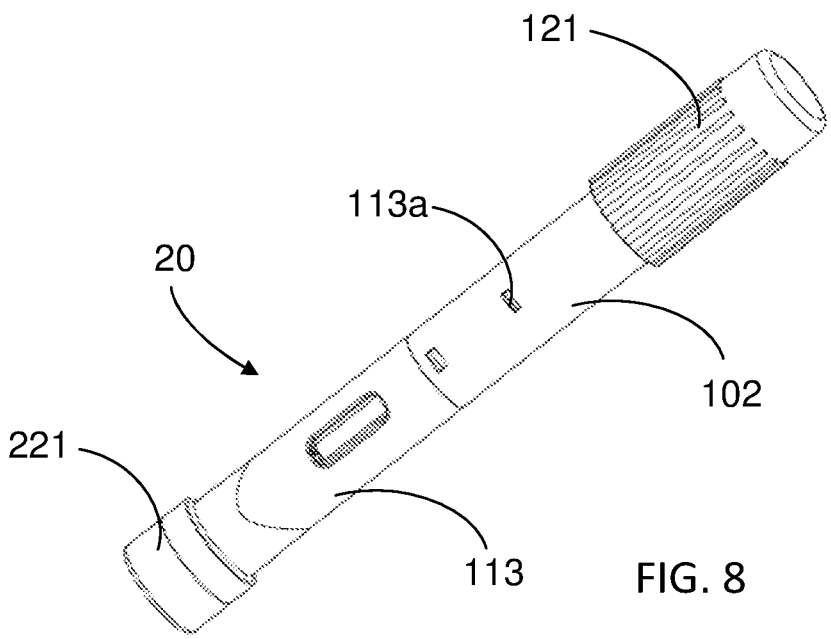

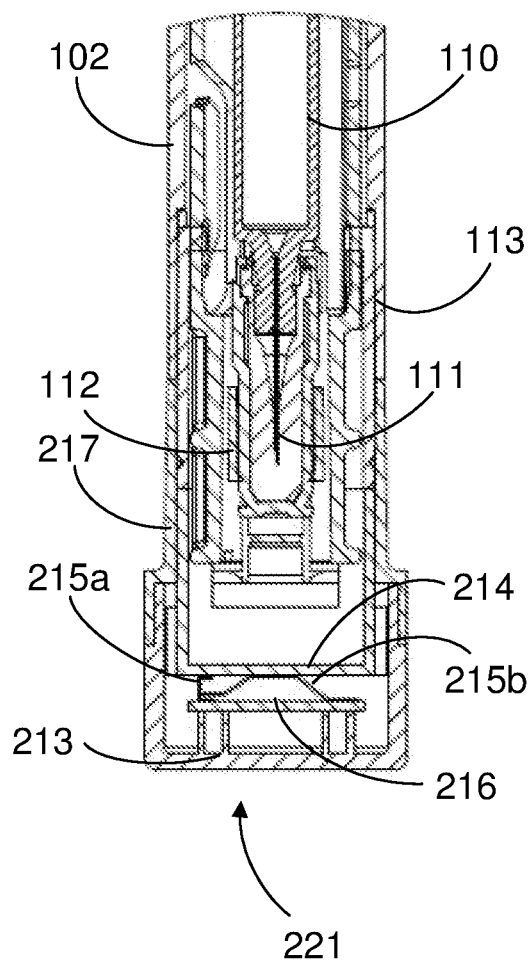
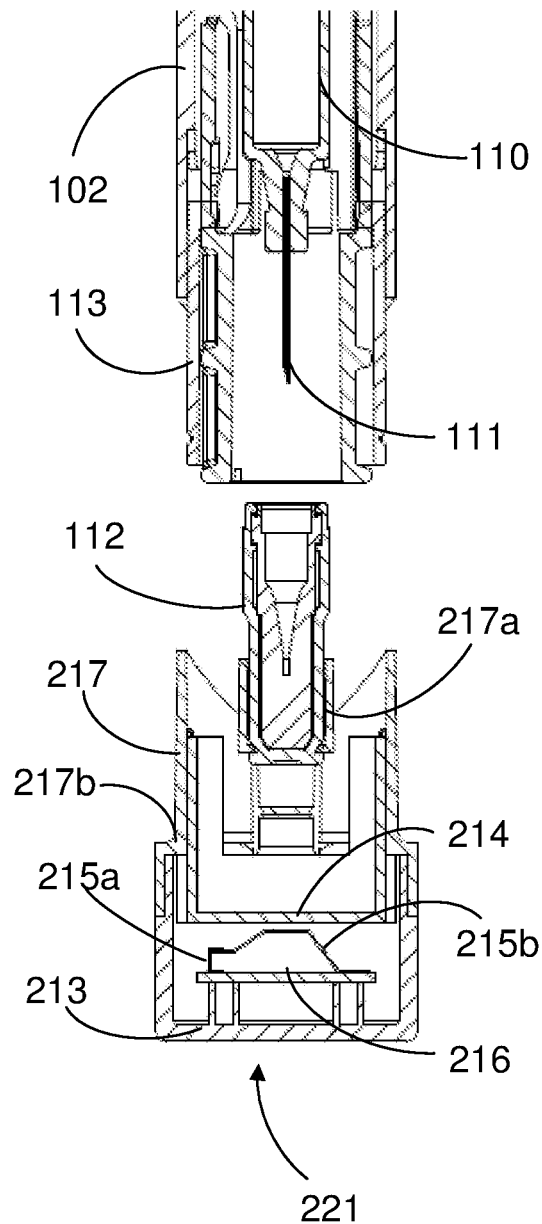

DRUG DELIVERY DEVICE

CROSS-REFERENCE TO RELATED APPLICATIONS

This application claims the benefit of U.S. Provisional Application Ser. No. 62/777,079, filed on Dec. 8, 2018.

BACKGROUND OF THE INVENTION

The present invention generally pertains to medical devices, and more particularly to drug delivery devices for delivering a drug into a body of a patient and outputting an electronic signal in response to such delivery.

Currently, biologic drugs account for more than half of all therapeutic drug candidates in pharmaceutical development pipelines. These biologic drugs need to be delivered through the parenteral route. As the parenteral therapeutic drugs become more and more popular, portable drug delivery devices, including pre-filled syringe and autoinjector device, for self-administration are expected to be widely used together with the parenteral therapeutic drugs (also referred as combination products). One type of such device is an autoinjector device. This type of device, when triggered by a user, automatically inserts into the user a needle of a pre-filled syringe that was disposed within the device housing, and then automatically injects a dose of medication through that inserted needle.

To ensure optimal patient treatment with biologic drug, it is essential for patients to comply with the medication regiments prescribed by their health care provider (HCP). Patient compliance can include any measure of a patient's conformance to a particular therapeutic drug delivery regimen or other indication as mandated by a health care provider or pharmaceutical manufacturer. More particularly, patient compliance measures can include the device status and medicament status, frequency of device usage, time of day, location where the device was activated, route of administration, functionality of the device once used. Understanding patient compliance with drug delivery devices can enhance the ability of a health care provider to effectively manage a patient's medication regimen, which can lead to improved patient outcomes. Patient compliance data can also be used to inform the device manufacturer about potential issues with the device. For example, data demonstrating poor compliance with a particular device may trigger a manufacturer to investigate the cause of poor compliance and/or change the design or functionality of the device to improve patient care and outcome. Similarly, knowing that patients complied with prescriptions is necessary to determine the efficacy of new medications in clinical trials. In clinical trials, healthcare providers rely on the patients to report medication compliance and on their truthfulness outside of the clinical setting. This reliance on patient truthfulness in taking the prescribed medication regiment can be a significant risk in clinical trials, where the investigative new drug's efficacy, benefits and other results depend heavily on the patients' compliance with the prescribed medication regiment.

Some prior arts utilize physical and electronics journals to keep track of patient medication regiment. In addition, other prior art consist of electronic reminders to remind patients to take their medication. Both of these systems are depended on patient truthfulness and compliance, and are only marginally effective. A healthcare provider will not be able to tell if, for example, a patient simply fill in their journals right before going in to see their doctor to show compliance, when the patient had not been compliant. With the electronic reminders the patient may simply silence the alarms without actually using the medication.

Additionally, some known drug delivery systems that combine a drug delivery device and an electronic system to assist the user in setting the proper dosage and/or maintaining a compliance log. Such known drug delivery systems and the accompanying electronic systems can be large and therefore not conveniently carried by the user. Such known drug delivery systems and the accompanying electronic systems can also be complicated to use and/or expensive to manufacture. Some other mechanical based drug delivery devices include add-on electronic adaptor to communicate the injection events. However, those add-on adaptors often alternate the exterior shape and size of the original mechanical based drug delivery device. Moreover, those add-on adaptors requires extra step(s) for user to activate (wake-up) the adaptors before use. Consequently, the user experience with the original device may be compromised.

In summary, there exists a need for an innovative device to capture the injection event and other confirmation information and to transmit such information, for example, wirelessly, to ensure patient compliance, in an easy and passive way.

SUMMARY OF THE INVENTION

In one form thereof, this invention presents drug delivery devices, for example, autoinjector devices or pre-filled syringes, that can generate wireless communications, through a detachable device unit, for example, a component or sub-assembly of the devices, with other communication devices as remote receivers, such as smart phone or smart watch. In some embodiments, the devices herein are able to creating a signal associated with a characteristic of an event of the drug delivery devices and then sending a wireless signal accordingly.

The invention employs the detachment of at least one component or sub-assembly (unit) of the drug delivery devices, within a wireless signal communication system, whereby the component or sub-assembly (unit) are embedded with wireless signal generation and transmission capabilities. When the the component or sub-assembly (unit) is detached from the drug delivery devices by the user before injection, the wireless signal generation and transmission capabilities are activated to establish an operating wireless communication system, together with other communication devices as remote receivers, for example, smart phone or smart watch.

In this invention, the detachment of the component or sub-assembly (unit), such as an activation protection cap or a syringe needle shield remover, creates a closed circuit, together with microprocessor, which is designed to generate wireless communication signals. For example, when a syringe needle shield remover is detached from a pre-filled syringe or an autoinjector device in order to remove a needle shield and expose an injection needle for injection, an electronic circuit in the syringe needle shield remover is closed and connected, the sensors and microprocessor embedded in the electronic circuit become operable to process and transmit signals for the wireless communication system. The wireless transmission system may include a Bluetooth chip and Bluetooth antenna or any other wireless transmission elements. In the component or sub-assembly (unit), there may be other sensors that detect various characteristics of the drug delivery.

To ensure that the system would not be unintentionally activated prior to a successful drug delivery, the electronic circuit is kept disconnected and open by a physical switch that is at off status before use. During use, when the component or sub-assembly (unit) is detached from the drug delivery device by the user, the electronic circuit is connected and closed to form a complete and operable wireless transmission system, which captures and/or transmits the drug delivery information.

One advantage of the present invention is that it employs the detachment of component or sub-assembly (unit) from the drug devices to activate the signal processing and wireless communication. At the same time, the detachment of component or sub-assembly (unit) is an essential step to use the drug delivery device, even in the case that no wireless communication is needed. This essential step can be, for example, removing a needle shield from a pre-filled syringe or an autoinjector device. Therefore, unlike other approaches for generating wireless communication signals, the present invention has no extra burden to the user compared with using the drug delivery device without wireless communication capability. Moreover, all the electronic elements are placed within the component or sub-assembly (unit) to be detached. The addition of the wireless communication capability has very minimum impact to the user interface designs of normal mechanical drug delivery devices.

Another advantage of the present invention is that detecting the completion of drug delivery is realized by detecting a specific sound frequency while the sound sensor for such event isn't attached to the drug delivery device.

Another advantage of the present invention is that the system in this invention is capable of reminding user to use the device as soon as possible after the injection needle is exposed to open air. This is important because the injection needle is sterile during storage. Once the injection needle is expose to open air before injection, the user needs to insert the injection needle as soon as possible to reduce the possibility of injection related infection.

Another advantage of the present invention is that the system in this invention is capable of in-directly measuring the temperature of the medication to be delivered. Sometime, the temperature of the medication is critical for optimal user experience because the medication in cold temperature may have high viscosity and cause slow or painful injection.

BRIEF DESCRIPTION OF THE DRAWINGS

The figures are schematic and simplied for clarity, and they just show details, which are essential to the understanding of the invention, while other details are left out. Throughout, the same reference numerals are used for identical or corresponding parts. Some embodiments are illustrated by way of example and not limitation in the figures of the accompanying drawings in which:

FIG. 2 is a cross-sectional view of the drug delivery device according to the invention;

FIG. 3 is a detailed cross-sectional view of the drug delivery device according to the invention;

FIGS. 6 and 7 are detailed cross-sectional views showing the operation mechanism of the activation protection cap of the drug delivery device of according to the invention.

FIG. 8 is a perspective view of an alternative design of the drug delivery device according to the invention;

FIGS. 11 and 12 are detailed cross-sectional views showing the operation mechanism of the syringe needle shield remover of the alternative design of the drug delivery device according to the invention.

DETAILED DESCRIPTION OF THE INVENTION

Figure 1:
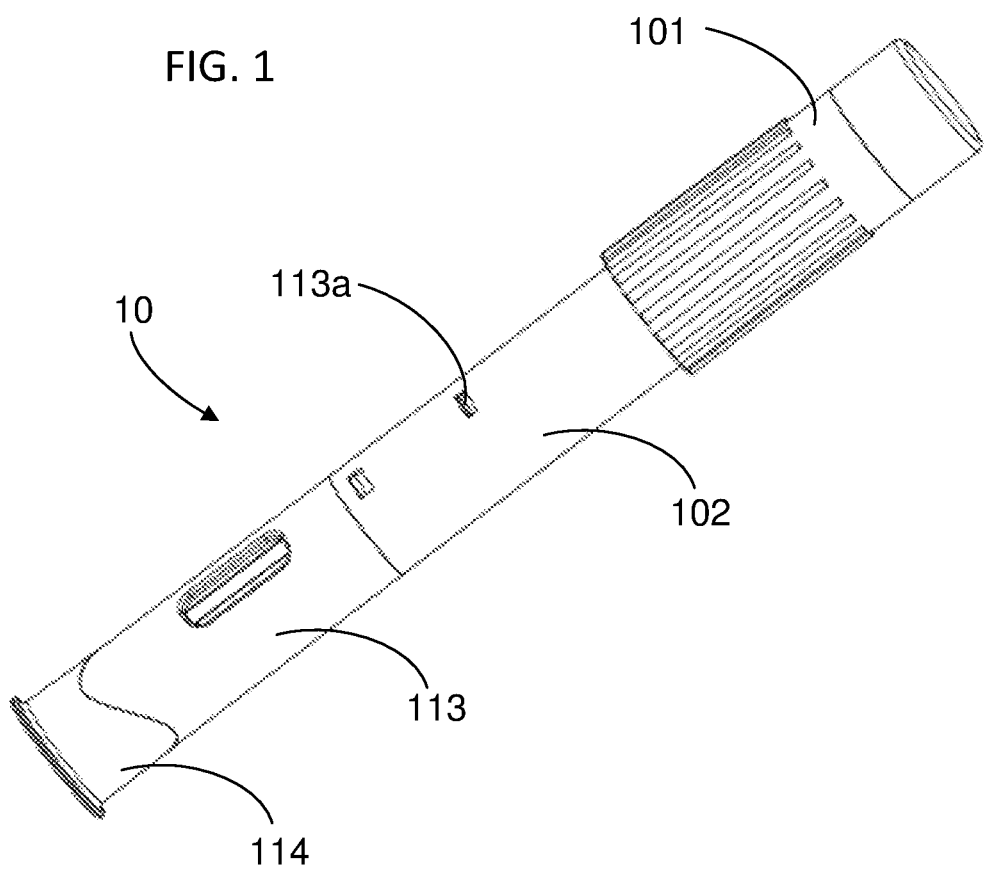
FIG. 1 is a perspective view of a drug delivery device according to the invention.

The present invention will become more fully understood from the detailed description given hereinbelow and the accompanying drawings which are given by way of illustration only, and thus, are not limitive of the present invention, and wherein:

The apparatus and methods presented herein can be used for delivering any of a variety suitable therapeutic agents or substances, such as dug, into a patient. Initially it may be convenient to define that, the term "distal end" is meant to refer to the needle end of the drug delivery device inserted into the patient, whereas the term "proximal end" is meant to refer to the end opposite to the "distal end" along the longitudinal axis of the device body. The words "upper", "lower", "right" and "left" designate directions in the drawings to which reference is made. The words "inward" and "outward" refer to directions toward and away from, respectively. The words "interior" and "exterior" refer to locations inside and outside, respectively.

In the patent drawings, FIGS. 1 and 2 illustrate the construction and function mechanism of an drug delivery device, autoinjector device 10. The autoinjector device 10 comprises an activation protection cap 101, an upper housing 102, a lower housing 113 and a syringe needle shield remover 114. Except the activation protection cap 101, all other components in the autoinjector device 10 contains no electronic element. In the autoinjector device 10, a syringe body 110 functions as a medication container to contain medication. An elastomeric movable piston 104 is placed inside the syringe body 110 for sealing the filled medication. In this embodiment, the medication outflow pathway is through an injection needle 111. There is a needle shield 112 that is used to cover the injection needle 111 and keep the injection needle 111 sterile before use. A push rod 103 is placed to apply pushing force on the movable piston 104. An activation button 105 is used to activate an automatic injection of the autoinjector device. An activation protection cap 101 is used to protect the activation button 105 from being accidentally activated. Before injection, the activation protection cap 101 is detached from the autoinjector device 10 so that the user can have access to the activation button 105. The needle shield 112 is also removed to expose the injection needle 111 by using the syringe needle shield remover 114. During injection, the activation button 105 is pushed toward to the distal end of the autoinjector device 10, a distally-directed tapered actuation feature on the activation button 105 releases a releasable latch mechanism formed between the push rod 103 and the upper housing 102. The push rod 103 is released and a driving spring 106 drives the push rod 103 to move toward to the distal end of the autoinjector device 10 in order to push the movable piston 104 toward to the distal end of the autoinjector device 10. Consequently, the medication in the syringe body 110 is injected from the device through the injection needle 111 into patient's body.

As illustrated in FIG. 3, there is a cantilever beam feature 103a on the push rod 103. The location of the cantilever beam feature 103a is configured to pass over a protrusion feature 113a on the lower housing 113 at the end of medication injection, i.e. the push rod 103 moves the elastomeric movable piston 104 to the distal end of the syringe body 110, driven by the driving spring 106. When the cantilever beam feature 103a passes over the inward protrusion feature 113a, it produces a vibration induced audible sound caused by the bending and reflecting of the cantilever beam feature 103a. The frequency and loudness of the audible sound generated by the cantilever beam feature 103a can be specifically configured to be distinguishable from background noise during use, by changing the shape, size and material modulus of the cantilever beam feature 103a. Other than being an integrated part of the push rod 103, the cantilever beam feature 103a may also be a separate component with different material of construction and be assembled together the push rod 103. The same sound generating mechanism can also be used for manual syringe (a pre-filled syringe) with a push rod. For the pre-filled syringe, an inward protrusion feature can be integrated on the finger flange or backstop of the syringe and a cantilever beam feature can be integrated on the push rod of the syringe. As is further described below, this functionality can be used together with other embodiments of the present invention.

Figure 4:
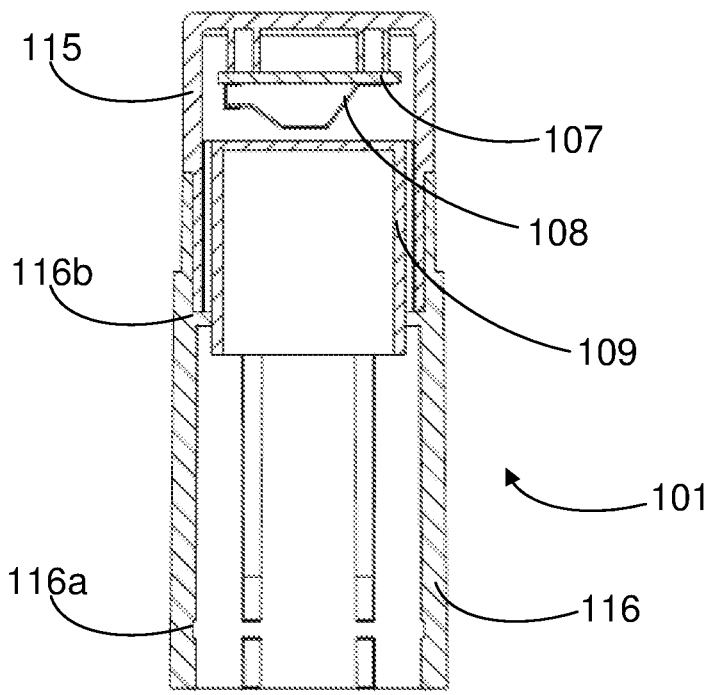
FIG. 4 is a cross-sectional view of an activation protection cap of the drug delivery device of according to the invention.
Figure 5:
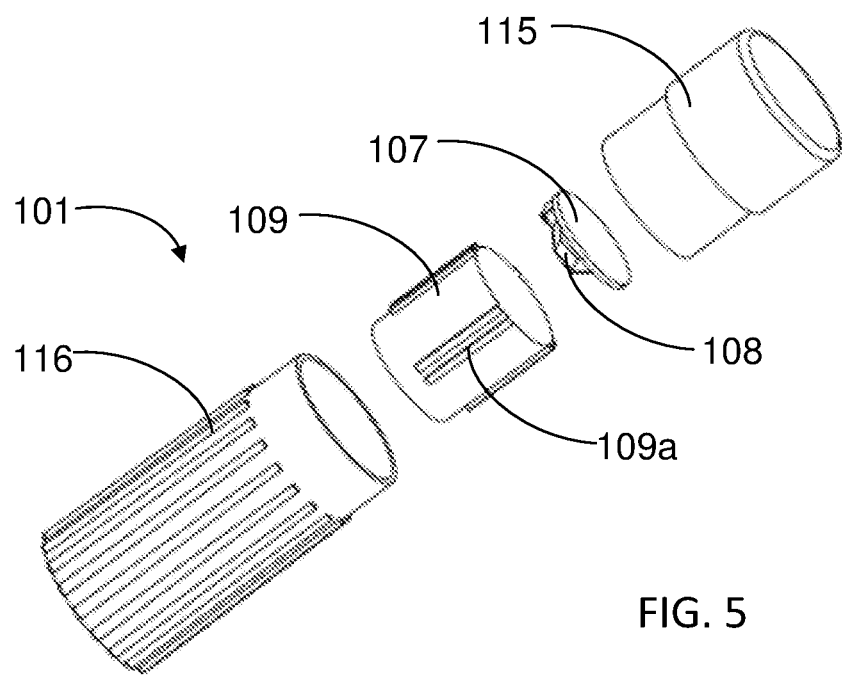
FIG. 5 is an exploded view of the activation protection cap of the drug delivery device of according to the invention.

FIGS. 4-7 illustrate the construction and function mechanism of the activation protection cap 101 according to the invention. With reference to FIGS. 4 and 5, the activation protection cap 101 includes a movable cylinder 109, a circuit board 107 with a microprocessor and other electronic components, an electronic on-off switch 108, an upper cap body 115 and a lower cap body 116. The upper cap body 115 and the lower cap body 116 may be jointed together by gluing or welding. The movable cylinder 109 can move along the longitudinal axis of the activation protection cap 101. The activation protection cap 101 is attached on the autoinjector device 10 through a snap-fit engagement formed between a bump feature 102a on the upper housing 102 and a recess feature 116a on the lower cap body 116. Other types of engagements, such as thread engagement, can also be used herein. FIGS. 6 and 7 show the mechanism of the activation of wireless communication. As shown in FIGS. 6 and 7, the electronic on-off switch 108 has two switch components made by conductive metal sheet, 108a and 108b, wherein the switch component 108b has springiness. FIG. 6 shows the status of the activation protection cap 101 before use. In FIG. 6, the activation protection cap 101 is assembled on the autoinjector device 10. The movable cylinder 109 is landed on the shoulder 102a of the upper housing 102 and thus pushes the switch component 108b upward to have the switch component 108b separated from the switch component 108a. Therefore, the switch 108 is at off position and the electric circuit is open and not connected. The microprocessor on the circuit board 107 is non-operational. FIG. 7 shows the status of the activation protection cap 101 after the activation protection cap 101 is detached. When the engagement between the activation protection cap 101 and the upper housing 102 is removed, the movable cylinder 109 is free to move downward, driven by the switch component 108b. As the result, the switch component 108b moves back to the unrestrained stage and connects with the switch component 108a. Then, the switch 108 is at on position and the electric circuit is closed and connected. Once the electric circuit is closed and connected. The microprocessor on the circuit board 107 becomes operational. The components on the circuit board 107, such as Bluebooth chip, will start to generate wireless signal. The wireless signal can be transmitted to smart phone or smart watch. The signal can inform user or caregiver that the device is ready to use, as well as additional information related to the current device status. Other signals, for example, device use timing, can also be recorded and processed. Other signal forms, for example, from light source (Light-emitting diode, LED) or sound speaker, can also be generated as status indicator or alarm. If light signal is desired, the upper cap body 115 may be made of transparent material so that the light generated by lighting source on the circuit board 107 can be visible. When the activation protection cap 101 is detached from the autoinjector device 10, the downward movement of the movable cylinder 109 may be limited when a rib feature 109a on the movable cylinder 109 lands on an inward projected shoulder feature 116b on the lower cap body 116. Therefore, the movable cylinder 109 won't fall out from the activation protection cap 101 after the activation protection cap 101 is detached from the autoinjector device 10. This design also enable the re-use of the activation protection cap 101 for another autoinjector device if necessary.

There may be a sound sensor, for example, a microphone, integrated on the circuit board 107. When the activation protection cap 101 is detached from the autoinjector device 10, the electric circuit on the circuit board 107 is closed and connected, and the sound sensor is ready to pick up sound signal. It indicates the end of injection when the sound frequency generated by the the cantilever beam feature 103a is matched. As described previously, the frequency of the audible sound generated by the cantilever beam feature 103a at the end of injection can be specifically configured to minimize false positive from external noise, e.g., human voices, household noises, picked up by the sound sensor and false positive from external movements. The microprocessor can be used to process the sound signal. Of course, the sound sensor hereby can also be used to detect other sound signals that indicate the completion of the drug delivery. Then, a wireless signal can be generated and sent to external remote receivers, such as smart phone or smart watch, and confirm the completion of injection.

Other than the sound sensor, a temperature sensor may also be integrated on the circuit board 107. The temperature sensor can be an infrared temperature sensor, a thermistor, a thermocouple or any known thermometer that can be read by the internal electronics. When the activation protection cap 101 is detached from the autoinjector device 10, the electric circuit on the circuit board 107 is closed and connected, and the temperature sensor starts to measure the temperature, which can be in-directly as a temperature measurement for the medication contained within the syringe body 110. At lower temperatures, the viscosity of the medication is typically higher and can cause slow or painful injection. Therefore, the medication contained within the syringe body 110 refrigerated for storage needs to be warmed to a proper injection temperature, e.g., room temperature, before injection. It is advantageous with the temperature sensor herein to inform user whether the drug delivery device is ready to injection for optimal user experience. Since the syringe body 110 is internal to the autoinjector device 10, the medication's temperature is expected to be different from the measurement from the temperature sensor embedded in the circuit board 107. Hence, there is a temperature offset between the internal syringe and the exterior of the autoinjector device 10. This temperature offset can be determined by experimentation and calibration and then incorporated into the signal process logic in the microprocessor in order to correlate the temperature of medication and the temperature measured by the temperature sensor in the activation protection cap 101.

Figure 9:
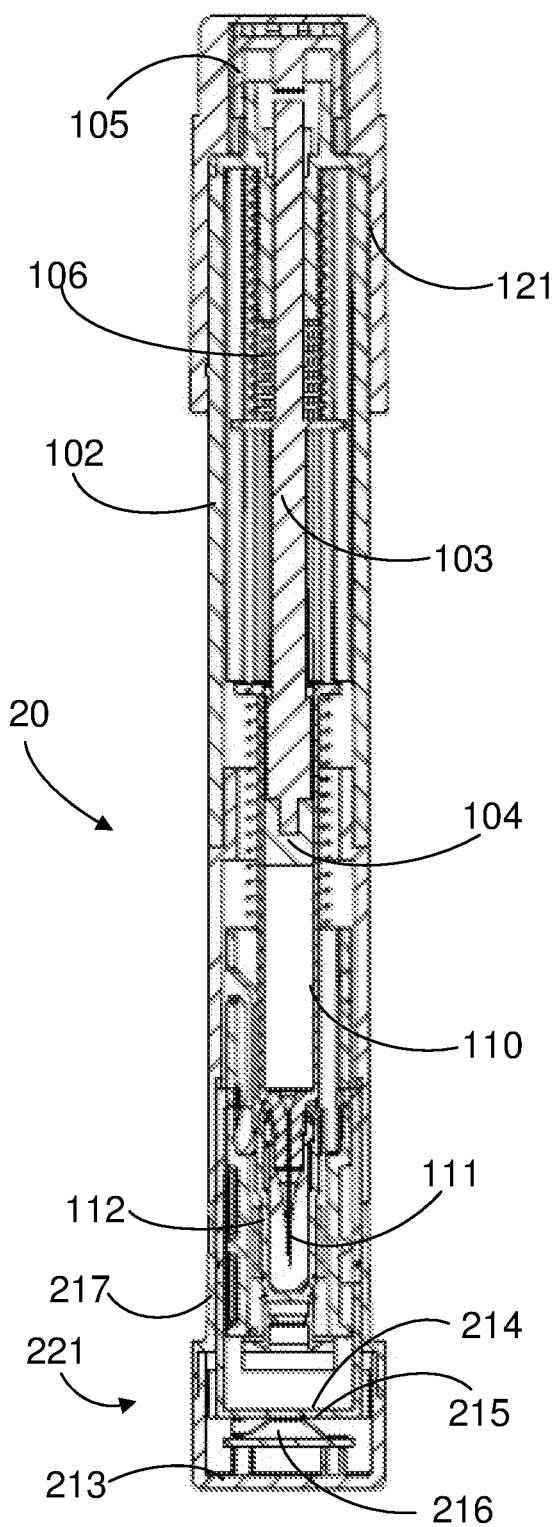
FIG. 9 is a cross-sectional view of the alternative design of the drug delivery device according to the invention.
Figure 10:
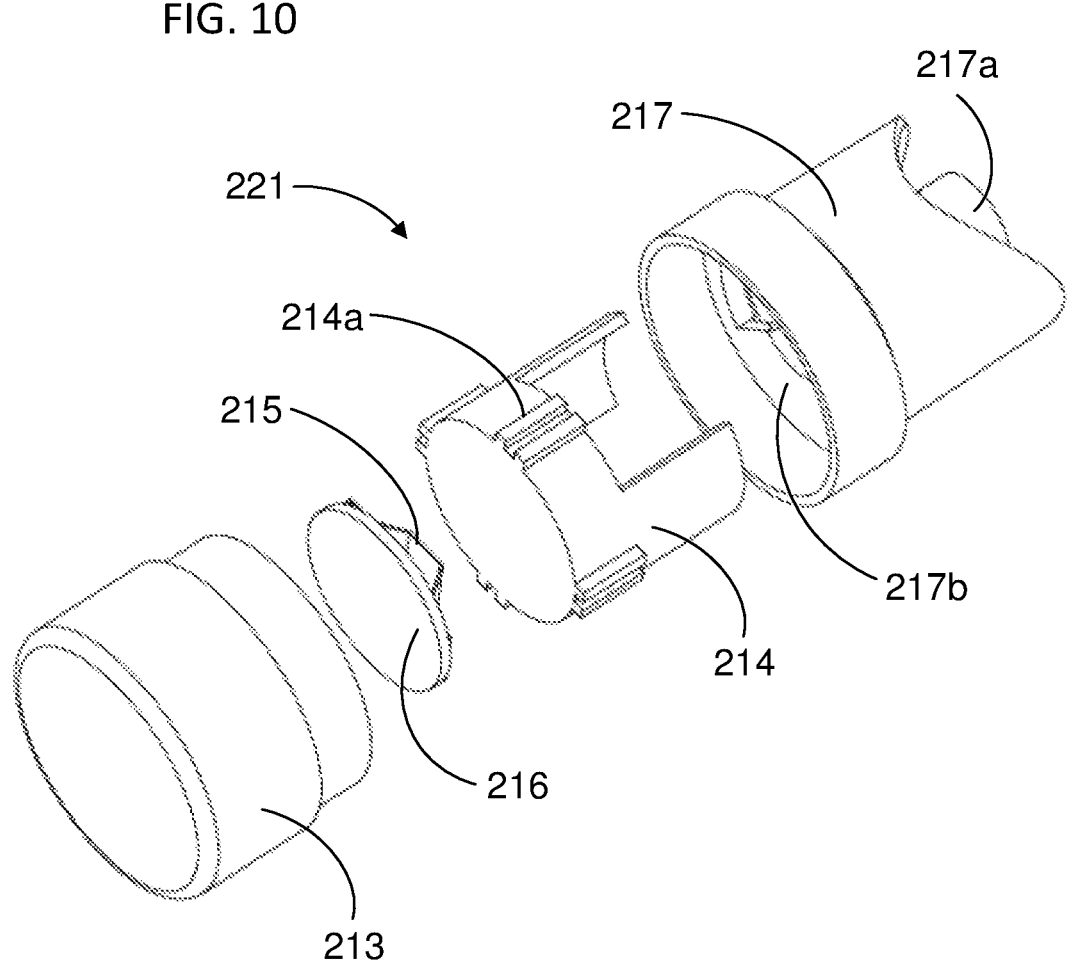
FIG. 10 is an exploded view of a syringe needle shield remover of the alternative design of the drug delivery device of according to the invention.

In the patent drawings, FIGS. 8 and 9 illustrate the construction and function mechanism of an drug delivery device, autoinjector device 20. In autoinjector device 20, rather than the activation protection cap 101, a regular activation protection cap 121 is used. A needle shield remover 221 with wireless communication capabilities is used herein to remove the needle shield 112, rather than the regular syringe needle shield remover 114 used in the autoinjector device 10. With reference to FIGS. 9 and 10, the needle shield remover 221 includes a movable cylinder 214, a circuit board 216 with a microprocessor and other electronic components, an electronic on-off switch 215, an upper remover body 217 and a lower remover body 213. The upper remover body 217 and the lower remover body 215 may be jointed together by gluing or welding. The movable cylinder 214 can move along the longitudinal axis of the needle shield remover 221. FIGS. 11 and 12 show the mechanism of the activation of wireless communication. As shown in FIGS. 11 and 12, the electronic on-off switch 215 has two switch components made by conductive metal sheet, 215a and 215b, wherein the switch component 215b has springiness. FIG. 11 shows the status of the needle shield remover 221 before use. In FIG. 11, the needle shield remover 221 is assembled on the autoinjector device 10. The movable cylinder 214 is landed on the lower housing 113 and push the switch component 215b downward and have the switch component 215b separated from the switch component 215a. Therefore, the switch 215 is at off position and the electric circuit is open and not connected. The microprocessor on the circuit board 216 is non-operational. FIG. 12 shows the device after the needle shield remover 221 is detached. In FIG. 12, the engagement between the needle shield remover 221 and the lower housing 113 is removed. A gripping feature 217a on the upper remover body functions to remove the needle shield 112 from the syringe body 110 and expose the injection needle 111 for injection. The movable cylinder 214 is free to move upward. Therefore, the component 215b moves back to the unrestrained stage (gap between the switch component 215b and the movable cylinder 214 shown in FIG. 12 is for descript purpose) and is connected with component 215a. Then, the switch 215 is at on position and the electric circuit is closed and connected. Once the electric circuit is closed and connected. The microprocessor on the circuit board 216 becomes operational. The components in the circuit board 216, such as Bluebooth chip, will start to generate wireless signal. The wireless signal can be transmitted to smart phone or smart watch. The signal can inform user or caregiver that the device has been activated. Signals about device use timing can also be recorded and processed.

There may also be a sound sensor, for example, a microphone, integrated on the circuit board 216, in such a way like previously described for autoinjector device 10. The sound sensor may be used to detect the completion of drug delivery. This design also works for manual syringe, for example, pre-filled syringe. In the situation for manual syringe, if a sound signal can be generated when user manually pushes a push rod to the distal end of the syringe, a sound sensor in a detachable unit, like the needle shield remover 221, can detect the completion of drug delivery.

Additional logic can be put into the microprocessor on the circuit board 216 to remind the user, with an alarm in light and/or sound signal forms, to start the injection if the injection is not completed after the needle shield remover 221 is detached and a predetermined time period elapses. The predetermined time period may be monitored by a real time clock (RTC) connected to the microprocessor on the circuit board 216, which is employed to measure the time elapsed after the needle shield remover 221 is detached from the autoinjector device 10. This is important because the user needs to insert the injection needle as soon as possible to reduce the possibility of injection related infection after the injection needle is expose to open air.

When the needle shield remover 221 is detached from the autoinjector device 20, the upward movement of the movable cylinder 214 may be limited while a rib feature 214a on the movable cylinder 214 lands on an inward projected shoulder feature 217b on the upper remover body 217. Therefore, the movable cylinder 214 won't fall out from the needle shield remover 221 after the needle shield remover 221 is detached from the autoinjector device 20.

Figure 13:
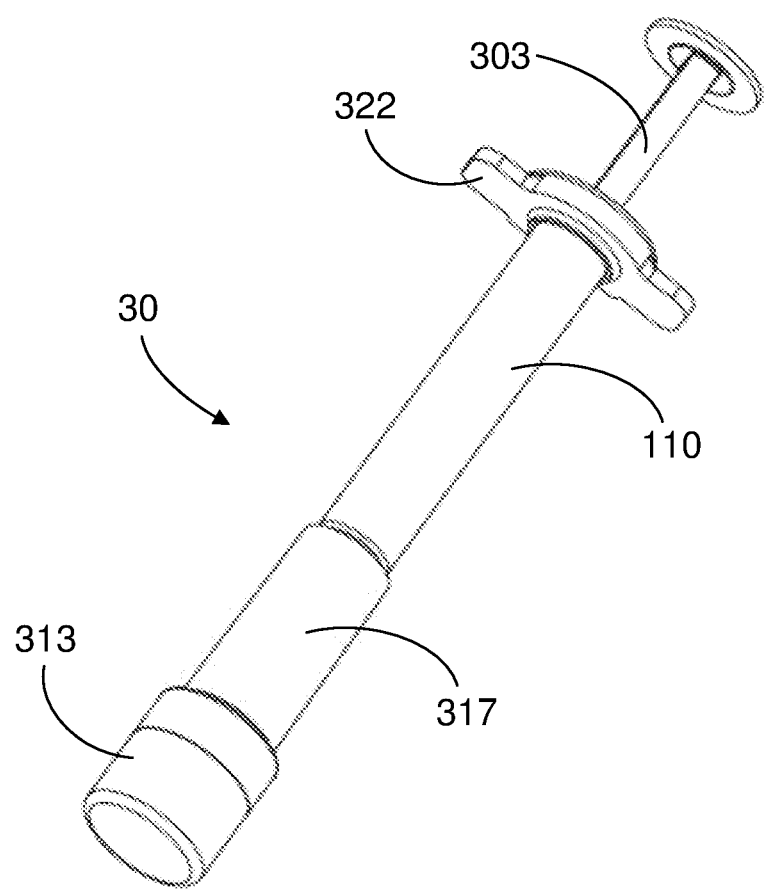
FIG. 13 is a perspective view of another drug delivery device according to the invention.

In the patent drawings, FIG. 13 illustrate the construction of an drug delivery device, a pre-filled syringe 30. In the pre-filled syringe 30, the medication contained in the syringe body 110 is delivered by user manually pushing a push rod 303 toward to the distal end of the pre-filled syringe 30. A backstop 322 is installed on the flange at the proximal end of the syringe body 110 to assist the manual injection. A needle shield remover 321 with wireless communication capabilities is used herein to remove the needle shield 112. The construction and operation mechanism of the needle shield remover 321 are as the same as those of the needle shield remover 221. The needle shield remover 321 includes a movable cylinder 314 (not shown), a circuit board 316 with a microprocessor and other electronic components (not shown), an electronic on-off switch 315 (not shown), an upper remover body 317 and a lower remover body 313. When the needle shield remover 321 is assembled on the pre-filled syringe 30, the switch 315 is at off position and the electric circuit on the circuit board 316 is open and not connected. When the needle shield remover 321 is detached from the pre-filled syringe 30, the switch 315 is at on position and the electric circuit on the electric board 316 is closed and connected.

The present invention may also include to an APP in a smart device adapted to pair with the drug delivery devices described above, wherein the smart device displays a graphical user interface (GUI) to a user. The APP may display a successful injection message to a user, an instruction to hold the drug delivery device at the injection site for a predetermined time duration and/or an instruction to discard the drug delivery device. The APP may also display alarm if necessary.

All the features in the above embodiments and design concepts herein can be inter-changed and combined to generate new device designs. Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A drug delivery device comprising:
   a medication container containing medication for delivery and having a distal end; and
   a detachable unit having an electronic circuit with a microprocessor, wherein the electronic circuit is open when the detachable unit is assembled on the drug delivery device; and the electronic circuit is closed when the detachable unit is detached from the drug delivery device.

2. The drug delivery device according to claim 1, wherein the detachable unit further comprising a wireless transmission unit, in the electronic circuit, to generate a wireless signal.

3. The drug delivery device according to claim 2, wherein the wireless signal is received by a remote receiver.

4. The drug delivery device according to claim 1, further comprising a sound generating means to produce sound at the end of medication delivery; and a sound sensor placed in the detachable unit to detect the sound produced at the end of medication delivery.

5. The drug delivery device according to claim 1, wherein the detachable unit further comprising a real time clock to measure the time elapsed after the detachable unit is detached from the drug delivery device.

6. The drug delivery device according to claim 5, wherein the microprocessor determines that a predetermined time period has elapsed.

7. The drug delivery device according to claim 1, wherein the detachable unit further comprising a temperature sensor to measure a temperature of the detachable unit.

8. The drug delivery device according to claim 7, wherein the detachable unit further comprising a logic embedded in the microprocessor to correlate a temperature of the medication and the temperature measured by the temperature sensor in the detachable unit.

9. The drug delivery device according to claim 1, wherein the medication container is a syringe with a needle.

10. The drug delivery device according to claim 9, wherein the medication in the medication container is sealed by a movable piston.

11. The drug delivery device according to claim 10, wherein the movable piston is pushed toward to the distal end of the medication container by a push rod, during the medication delivery.

12. The drug delivery device according to claim 11, wherein the push rod is driven by a spring, and the spring is released by an activation button.

13. The drug delivery device according to claim 12, wherein the detachable unit is a protection cap to protect the activation button from being accidentally activated.

14. The drug delivery device according to claim 12, wherein the protection cap is re-usable.

15. The drug delivery device according to claim 9, wherein the needle is covered by a needle shield, and the needle is sterile before the needle shield is removed.

16. The drug delivery device according to claim 15, wherein the detachable unit is a remover to remove the needle shield from the needle.

17. The drug delivery device according to claim 1, further comprising an on-off switch in the electronic circuit.

18. The drug delivery device according to claim 1, wherein the detachable unit further comprising a light source to generate a light signal.

19. The drug delivery device according to claim 1, wherein the detachable unit further comprising a sound speaker to generate a sound signal.

* * * * *